(12) United States Patent
Jooste et al.

(10) Patent No.: US 10,252,140 B1
(45) Date of Patent: *Apr. 9, 2019

(54) ACTIVITY METRIC CALCULATION FOR WEARABLE DEVICES

(71) Applicant: Verily Life Sciences LLC, Mountain View, CA (US)

(72) Inventors: Sarel Kobus Jooste, Novato, CA (US); David Andrew Gibson, Mountain View, CA (US); Mark Murphy, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/951,292

(22) Filed: Apr. 12, 2018

Related U.S. Application Data

(63) Continuation of application No. 14/332,191, filed on Jul. 15, 2014, now Pat. No. 9,950,236.

(51) Int. Cl.
*A63B 71/06* (2006.01)
(52) U.S. Cl.
CPC .................... *A63B 71/06* (2013.01)
(58) Field of Classification Search
CPC . A63B 71/00; A63B 71/0605; A63B 71/0616; A63B 24/00; A63B 24/0003; A63B 24/0006; A63B 24/0021; A63V 71/06
See application file for complete search history.

(56) References Cited

U.S. PATENT DOCUMENTS

| 7,927,253 | B2* | 4/2011 | Vincent | A63B 24/0021 |
| | | | | 482/9 |
| 8,001,472 | B2* | 8/2011 | Gilley | G06F 19/3418 |
| | | | | 715/716 |
| 8,579,767 | B2* | 11/2013 | Ellis | A61B 5/1038 |
| | | | | 482/8 |
| 9,950,236 | B1 | 4/2018 | Jooste et al. | |
| 2003/0093248 | A1* | 5/2003 | Vock | A42B 3/0433 |
| | | | | 702/188 |
| 2004/0102931 | A1* | 5/2004 | Ellis | A61B 5/1038 |
| | | | | 702/188 |
| 2006/0136173 | A1* | 6/2006 | Case, Jr. | A63B 24/00 |
| | | | | 702/182 |

(Continued)

*Primary Examiner* — Garrett K Atkinson
(74) *Attorney, Agent, or Firm* — McDonnell Boehnen Hulbert & Berghoff LLP

(57) ABSTRACT

A wearable device described herein includes a housing and a mount configured to mount the housing to an external surface of a wearer. The wearable device further includes one or more sensors configured to measure at least one physiological parameter of the wearer. The wearable device may obtain an activity metric that is based on at least one physiological parameter of the wearer measured by the one or more sensors and demographical data specific to the wearer. In some examples, the wearable may be configured to calculate the activity metric or a preliminary activity metric and to indicate the activity metric and/or preliminary activity metric to the wearer. In some examples, the wearable device may transmit the physiological parameter measurement to an external device and receive an indication of the activity metric from the external device.

20 Claims, 11 Drawing Sheets

(56) References Cited

U.S. PATENT DOCUMENTS

| | | | | |
|---|---|---|---|---|
| 2008/0076637 A1* | 3/2008 | Gilley | ................ | G06Q 10/0639 |
| | | | | 482/9 |
| 2008/0086318 A1* | 4/2008 | Gilley | ................... | G06Q 10/06 |
| | | | | 705/319 |
| 2009/0233771 A1* | 9/2009 | Quatrochi | .......... | A63B 24/0075 |
| | | | | 482/9 |
| 2010/0048358 A1* | 2/2010 | Tchao | ................. | G06F 19/3418 |
| | | | | 482/9 |
| 2014/0172135 A1* | 6/2014 | Eisner | ............... | G06F 15/17306 |
| | | | | 700/91 |

\* cited by examiner

ACTIVITY METRIC CALCULATION FOR WEARABLE DEVICES

CROSS-REFERENCE TO RELATED APPLICATIONS

This application is a continuation of U.S. patent application Ser. No. 14/332,191, filed Jul. 15, 2014, which is incorporated herein by reference.

BACKGROUND

Unless otherwise indicated herein, the materials described in this section are not prior art to the claims in this application and are not admitted to be prior art by inclusion in this section.

Computing systems such as personal computers, laptop computers, tablet computers, cellular phones, and countless types of Internet-capable devices are prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." For example, some wearable devices are wearable computing devices are wrist-mounted devices that can worn like a wrist watch.

SUMMARY

Some embodiments of the present disclosure provide a method that includes a wearable device obtaining a measurement of one or more physiological parameters related to a wearer of the wearable device. The method further includes the wearable device receiving from the external device an indication of an activity metric that is based on the obtained measurement and demographical data specific to the wearer.

Some embodiments of the present disclosure provide a wearable device that includes one or more sensors configured to measure physiological parameters related to a wearer of the wearable device and one or more processors. The one or more processors may be configured to cause the one or more sensors to obtain a measurement of at least one physiological parameter and obtain an activity metric, the activity metric being based on the obtained measurement and demographical data specific to the wearer.

Some embodiments of the present disclosure provide a method that includes a server compiling demographical data related to a plurality of wearers of wearable devices. The demographical data may include a plurality of categories. The method may further include the server receiving physiological parameter measurements from a plurality of wearable devices that include a given wearable device. The method may further include the server calculating an activity metric for the given wearable device based on at least one physiological parameter measurement received from the given wearable device and demographical data specific to a wearer of the given wearable device, and the server transmitting to the given wearable device an indication of the activity metric.

These as well as other aspects, advantages, and alternatives, will become apparent to those of ordinary skill in the art by reading the following detailed description, with reference where appropriate to the accompanying drawings.

DETAILED DESCRIPTION

Figure 1:
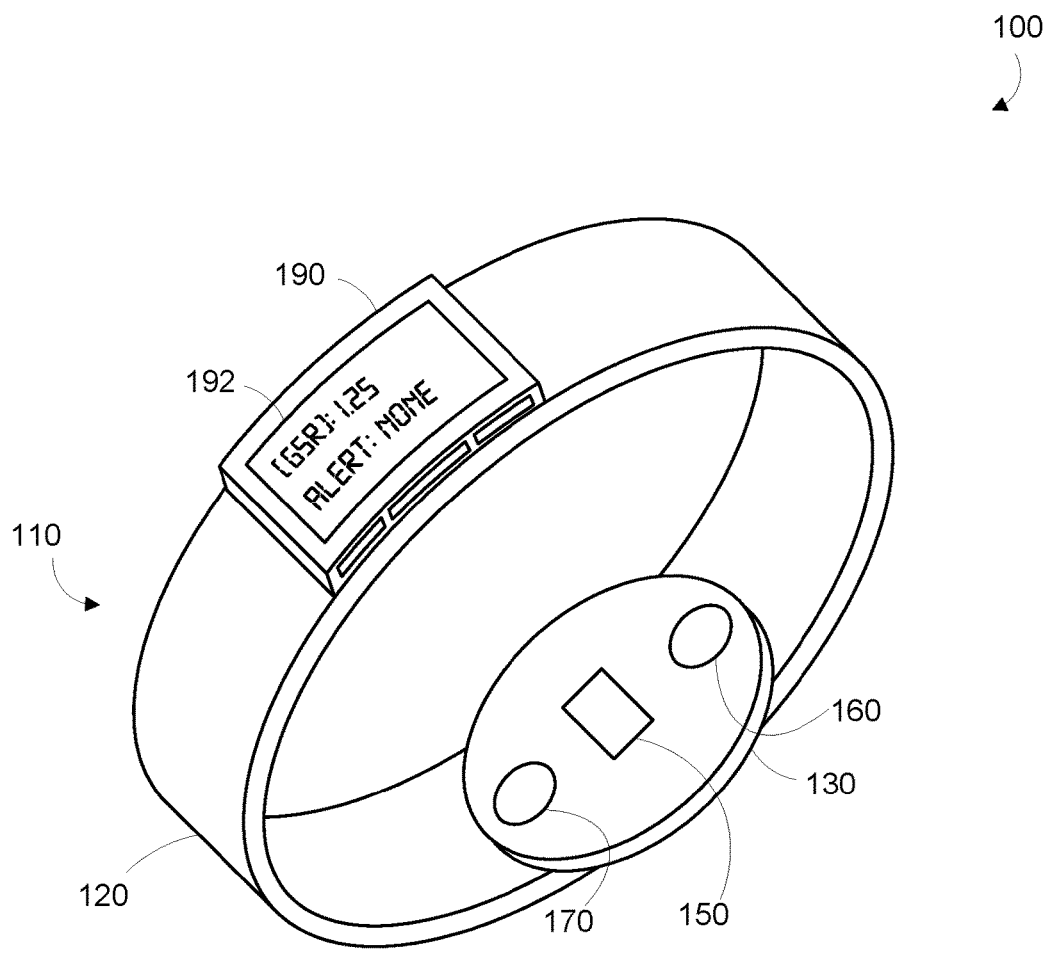
FIG. 1 is a perspective view of an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

A wearable device may be configured to measure one or more physiological parameters of the wearer of the wearable device. In some examples, the wearable device includes a housing (e.g., a water-resistant housing) and a mount (e.g., a band) that can mount the housing on a particular external body location, such as a wrist. The wearable device may further include one or more sensors configured to obtain measurements of the one or more physiological parameter measurement of the wearer. In addition, the wearable device may include one or more processors configured to obtain an activity metric that is based on a measurement obtained by the one or more sensors and demographical information specific to the wearer. The activity metric may be a numeric representation of the physiological parameter measurements and/or the type, duration, or intensity of physical activity engaged in by a wearer. To obtain the activity metric, the wearable device may calculate the activity metric (e.g., using the one or more processors) based on the measurement obtained by the one or more sensors and demographical information stored at the wearable device. Alternatively, the wearable device may receive the activity metric from an external device (e.g., a remote server).

In some examples, the wearable device may include a wireless communication interface that can transmit data to an external device, for example, using Bluetooth, ZigBee, WiFi, and/or some other wireless communication protocol. The data transmitted by the wireless communication interface may include data indicative of one or more physiological parameters measured by the device.

In some examples, the external device may be configured to calculate an activity metric based on the physiological parameter measurements received from a wearable device and demographical data specific to the wearer of the wearable device. Additionally or alternatively, the external device may determine where the physiological parameter measurements and/or the calculated activity metric ranks among other physiological parameter measurements or other activity metrics measured or calculated for other wearers with similar demographical data to the wearer. The external device may also be configured to transmit to the wearable device indications of the calculated activity metric and/or indications of determined rankings.

In some examples, the wearable device may include a user interface that is configured to provide user-discernible indications (e.g., visual, audible, and/or tactile indications) of one or more physiological parameters measured and/or determined by the device, as well as indications of activity metrics and/or rankings.

II. EXAMPLE WEARABLE DEVICES

A wearable device 100 can be configured to measure a plurality of physiological parameters of a person wearing the device. The term "wearable device," as used in this disclosure, refers to any device that is capable of being worn at, on or in proximity to an external body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 110, such as a belt, wristband, ankle band, etc. can be provided to mount the device at, on, or in proximity to the external body surface. In some embodiments, a mount could additionally or alternatively include an adhesive. For example, a mount could include an adhesive and could be configured such that it could be used to mount a wearable device to an external body surface of a wearer without wrapping around a part of the wearer (e.g., a limb). The mount 110 may prevent the wearable device 100 from moving relative to the body to ensure consistent contact between the wearable device 100 and the skin to enable consistent measurement of physiological parameters. In one example, shown in FIG. 1, the mount 110, may take the form of a strap or band 120 that can be worn around a part of the body.

A housing 130 is disposed on the mount 110 such that the housing 130 can be positioned on an external surface of the body. The housing 130 may house the data collection system 150, which may include detector 160 for detecting at least one physiological parameter, which could include any parameters that may relate to the health and/or activity level of the person wearing the wearable device. For example, the detector 160 could be configured to measure blood pressure, pulse rate, respiration rate, skin temperature, blood-oxygen level, etc. In some instances, detector 160 is configured to non-invasively measure one or more analytes in blood circulating in subsurface vasculature proximate to the wearable device. Detector 160 could also be configured to measure one or more environmental parameters, such as ambient temperature or humidity.

In a non-exhaustive list, detector 160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

In some examples, the data collection system 150 further includes a signal source 170 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter.

In some examples, the interrogating can be used to detect the binding of a clinically-relevant analyte to functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect.

In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. The interrogating signal may therefore be an electromagnetic radiation signal with a wavelength that penetrate the skin or other tissue and subsurface vasculature (e.g., a wavelength in the range of about 500 to about 1000 nanometers).

In some examples, the response signal detected by the detector 160 is a portion of the interrogating signal that has been transmitted through or reflected from subsurface vasculature. For instance, the response signal may be related to a level of oxygenation of hemoglobin and may be used to determine a blood-oxygen level. In some examples, the functionalized particles include a fluorophore, and the response signal is fluorescence radiation from the fluorophore that can penetrate the subsurface vasculature and tissue to reach the detector. The fluorescence radiation may be related to binding of the clinically-relevant analyte to the functionalized particles.

In some cases, an interrogating signal may not be used to measure one or more of the physiological parameters and, therefore, the wearable device 100 may not include a signal source 170. For example, functionalized particles can include an autofluorescent or luminescent marker, such as a fluorophore, that will automatically emit a response signal indicative of the binding of the clinically-relevant analyte to the functionalized particles, without the need for an interrogating signal or other external stimulus. In some examples, the functionalized particles may include a chemoluminescent marker configured to produce a response signal in the form of fluorescence radiation produced in response to a chemical reaction initiated, at least in part, to the binding of the target analyte to the particle.

In some examples, detector 160 and signal source 170 may be electrical contacts that protrude from the housing 130 so as to contact skin at the external surface of the body. In such examples, the Galvanic skin resistance (GSR) of the skin at the external surface of the body could be measured between the first and second electrical contacts 160, 170. Additionally, as electrical contacts, detector 160 and signal source 170 could be configured to interface with a charger or other device such that a rechargeable battery that powers the wearable device 100 could be charged through the electrical contacts.

The detector 160 and signal source 170 could be composed of an electrically conductive material, such as a metal or a combination of metals, or a nonmetal conductor. The detector 160 and signal source 170 could be composed of the same material or different materials. The detector 160 and signal source 170 could each be composed of a single material or could be composed of multiple materials. For example, detector 160 and signal source 170 could have a bulk composed of one material and a surface plating of another material. For example, detector 160 and signal source 170 could have a bulk composed of copper and a surface composed of gold or of gold alloyed with nickel and/or cobalt. The surface layer could be deposited by a number of methods familiar to one skilled in the art; for example, electroplating. Other compositions are possible, as well.

The detector 160 and signal source 170 could be spring loaded. That is, the electrical contacts could be configured to include one or more springs or other elements that could be reversibly compressed. The detector 160 and signal source 170 could be spring loaded in a direction perpendicular to an external surface of the body to which the housing 130 could be mounted. That is, detector 160 and signal source 170 could be spring loaded in order to improve and/or make more consistent an electrical connection between the electrical contacts and skin of the external body surface to which the housing 130 was mounted by the mount 110. Alternatively, detector 160 and signal source 170 could be fixed relative to housing 130.

The geometry of detector 160 and signal source 170 that protrude from the housing 130 could be configured to improve and/or make more consistent an electrical connection between the electrical contacts and skin of the external body surface to which the housing 130 was mounted by the mount 110. For example, the protruding aspects of the detector 160 and signal source 170 could be hemispherical, conical, parabolic, cylindrical, or shaped in some other manner. The detector 160 and signal source 170 could be flat or substantially flat plates (e.g., rectangular, triangular, or other-shaped plates protruding from the housing 130). The detector 160 and signal source 170 could have a faceted geometry. For example, the detector 160 and signal source 170 could be triangular, rectangular, or other-shapes pyramids. The protruding aspects of the detector 160 and signal source 170 could have, for example, a characteristic size (e.g., diameter of cylinders, cones, or hemispheres, width of rectangular prisms or plates, or some other measure of size) between 1 and 5 millimeters. Further, the protruding aspects of the detector 160 and signal source 170 could have an inscribed, cast, and/or pressed texture or pattern. Additionally or alternatively, the exposed aspects of the detector 160 and signal source 170 could be roughened mechanically, chemically, or by some other method. Other geometries, sizes, surface treatments, and other aspects of the configuration of the detector 160 and signal source 170 are anticipated.

The detector 160 and signal source 170 could be arranged a distance apart such that a GSR measured using the detector 160 and signal source 170 could have a desired property or properties. For example, the detector 160 and signal source 170 could be separated by a distance of between 1 and 50 millimeters, such as about 25 millimeters. The detector 160 and signal source 170 could be disposed on the housing 130 such that, if the housing 130 is mounted to a wrist of a wearer of the wearable device 100, the electrical contacts 160, 170 would be arranged on a line substantially parallel to the bones of the forearm of the wearer (i.e., the radius and ulna). Other distances and directions are also possible.

The housing 130 could be configured to be water-resistant. That is, the housing could be configured to include sealants, adhesives, gaskets, welds, press-fitted seams, and/or other joints such that the housing 130 is resistant to water entering an internal volume or volumes of the housing 130. Further, the interface between the housing 130 and the detector 160 and signal source 170 protruding from the housing 130 could be configured such that the combination of the housing 130 and the detector 160 and signal source 170 is water-resistant.

The data collection system 150 may include additional electronics (not individually shown in FIG. 1) configured to measure physiological parameters of the skin at an external surface of the body proximate to the housing 130, using the detector 160 and signal source 170 when the wearable device 100 is mounted to the external surface of the body. The electronics may include a GSR sensor configured to obtain a measurement relating to the GSR of the skin at the external surface of the body, via the detector 160 and signal source 170 when a rectifier disposed in the wearable device 100 is reverse biased. The GSR sensor could include a reference voltage source electrically connected to the detector 160 through a resistor having a reference resistance. The GSR sensor may also include a voltage sensor electrically connected to the detector 160. The reference voltage source generates a reference voltage relative to the signal source 170 and the voltage sensor measures a voltage between the detector 160 and signal source 170. A battery recharger could also be included in the electronics and electrically connected to the detector 160 through the rectifier.

A GSR of skin proximate to the detector 160 and signal source 170 could be determined based on a measurement relating to the GSR of the skin obtained using the GSR sensor when the wearable device 100 is mounted to the external surface of the body and when the rectifier is reverse biased. In some examples, the measurement relating to the GSR of the skin could include a measurement of the voltage between the detector 160 and signal source 170 and the GSR of skin proximate to the detector 160 and signal source 170 could be determined based on the measured voltage, the value of a reference voltage produced by a reference voltage source, a resistance of a reference resistor, and/or other factors. For example, the GSR could be determined by calculating a multiple of the reference resistance corresponding to the measured voltage divided by a difference, where the difference is the measured voltage subtracted from the reference voltage. Other methods of determining a GSR could be used, for example a lookup table relating measured voltages to GSR values.

The detector 160 and signal source 170 protruding from the housing 130 could additionally be used for other purposes. For example, electronics disposed in the wearable device 100 could be used to sense an electrocardiogram (ECG) signal, a Galvanic skin potential (GSP), an electromyogram (EMG) signal, and/or some other physiological signal present at the detector 160 and signal source 170. Additionally or alternatively, the detector 160 and signal source 170 could be used to detect the presence of a charging device or some other electronic system electrically connected to the detector 160 and signal source 170.

The data collection system 150 may include additional electronic components to measure additional physiological parameters, such as the type, duration, and intensity of physical activity engaged in by a wearer of the wearable device 100. In one example, these additional electronic components include one or more accelerometers or other motion sensors that are configured to measure movement of the wearable device 100, and thus measure movement of a wearer of wearable device 100. The one or more accelerometers may be configured to produce various output signals that, collectively, are indicative of the type and extent of movement of the wearable device. For example, when a wearer of wearable device 100 is running, the output signals produced by the one or more accelerometers may be characteristic of running. That is, the output signals may exhibit a particular pattern of voltage magnitudes that is unique to the activity of running. In another example, when a wearer of wearable device 100 is walking, the output signals produced by the one or more accelerometers may be characteristic of walking. That is, the output signals may exhibit a particular pattern of voltage magnitudes that is unique to the activity of walking and, therefore, different than a particular pattern of voltage magnitudes unique to, say, running. In other examples, the output signals produced by the one or more accelerometers may be characteristic of one of many different types of physical activities, such as walking, running, swimming, climbing steps, cycling, hiking, rowing, skiing, skating, and others. The data collection system 150 may periodically analyze these output signals to determine the type, duration, and intensity of physical activity engaged in by a wearer of wearable device 100 at any given time.

The wearable device 100 may also include a user interface 190 via which the wearer of the device may receive one or more recommendations or alerts generated from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication of the battery status of the device or an indication of any measured physiological parameters being measured by the device.

Figure 2A:
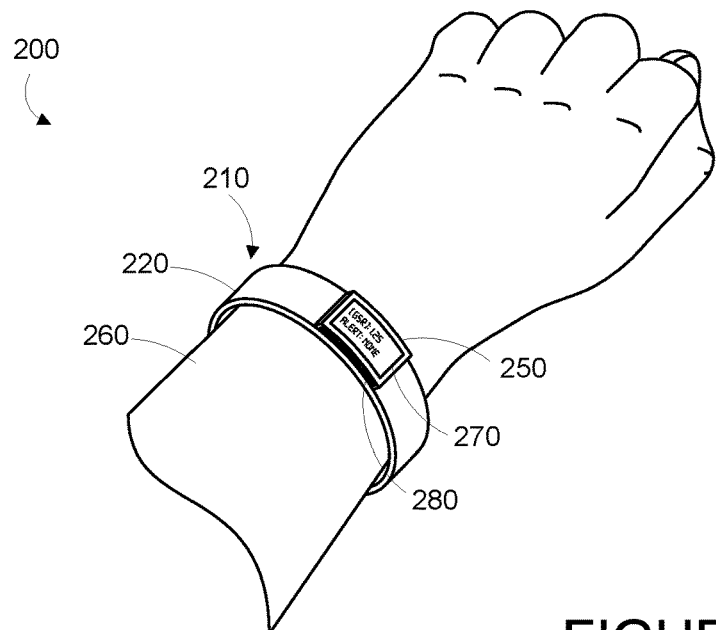
FIG. 2A is a perspective top view of an example wrist-mountable device, when mounted on a wearer's wrist.
Figure 2B:
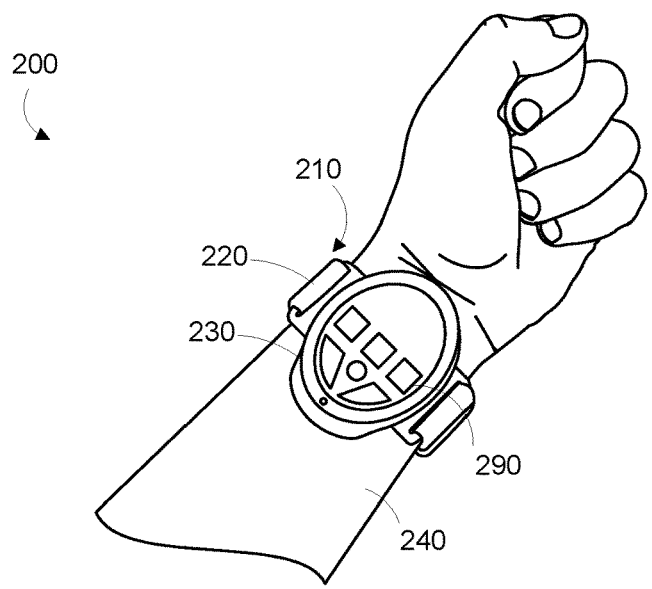
FIG. 2B is a perspective bottom view of the example wrist-mountable device shown in FIG. 2A, when mounted on a wearer's wrist.

In some examples, the wearable device is provided as a wrist-mounted device, as shown in FIGS. 2A, 2B, 3A-3C, 4A, 4B, 5 and 6. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a housing 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts generated by the operation of the wrist mounted device 200. Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the housing 230 may be located on the anterior side 240 of the wearer's wrist. However, other configurations are contemplated.

The display 270 may be configured to display a visual indication of the alert or recommendation and/or an indication of the status of the wearable device or an indication of measured physiological parameters being measured by the wrist mounted device 200. Further, the user interface 250 may include one or more buttons 280 for accepting inputs from the wearer. For example, the buttons 280 may be configured to change the text or other information visible on the display 270. As shown in FIG. 2B, housing 230 may also include one or more buttons 290 for accepting inputs from the wearer. The buttons 290 may be configured to accept inputs for controlling aspects of the wrist mounted device 200, such as initiating a GSR measurement period, or inputs indicating the wearer's current health and/or affect state (e.g., normal, anxious, angry, calm, migraine, shortness of breath, heart attack, fever, "flu-like" symptoms, food poisoning, etc.).

Figure 3A:
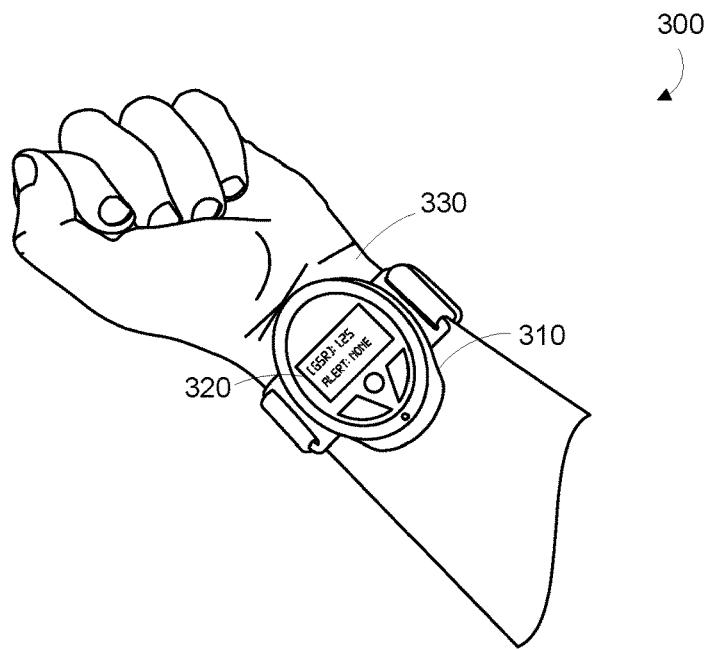
FIG. 3A is a perspective bottom view of an example wrist-mountable device, when mounted on a wearer's wrist.
Figure 3B:
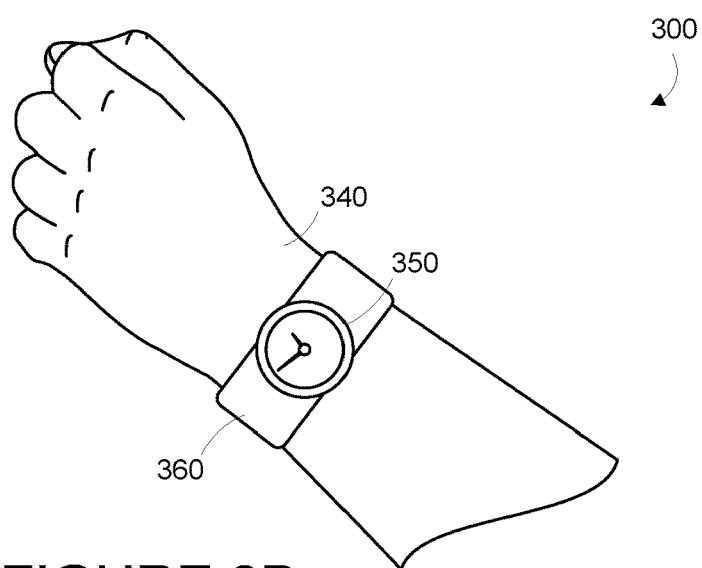
FIG. 3B is a perspective top view of the example wrist-mountable device shown in FIG. 3A, when mounted on a wearer's wrist.
Figure 3C:
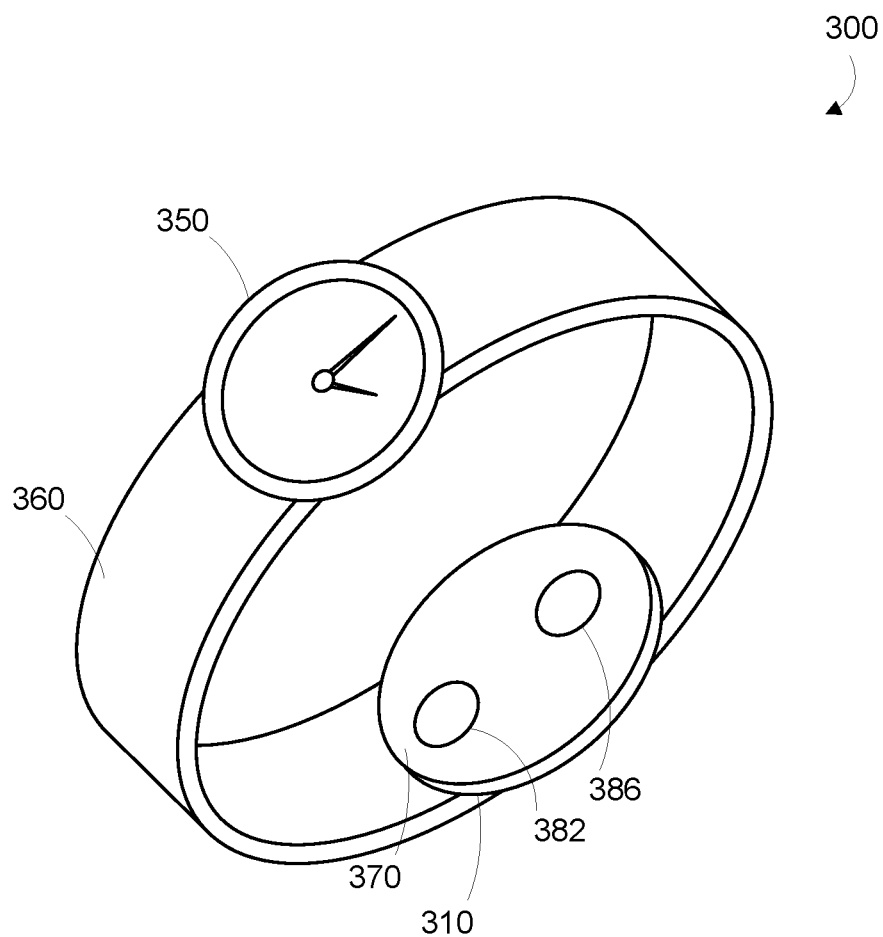
FIG. 3C is a perspective view of the example wrist-mountable device shown in FIGS. 3A and 3B.

In another example wrist-mounted device 300, shown in FIGS. 3A-3C, the housing 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the housing 310 is intended to be worn proximate to skin on an external surface of the wearer's body. A first electrical contact 382 and a second electrical contact 386 protrude from the inner face 370 of the housing 310 such that a measurement of one or more physiological parameters of skin proximate to the inner face 370 could be measured using the electrical contacts 382, 386 when the wrist-mounted device 300 was mounted to a wrist of a wearer. The electrical contacts 382, 386 could also be used to charge a battery of the wrist-mounted device 300.

Figure 4A:
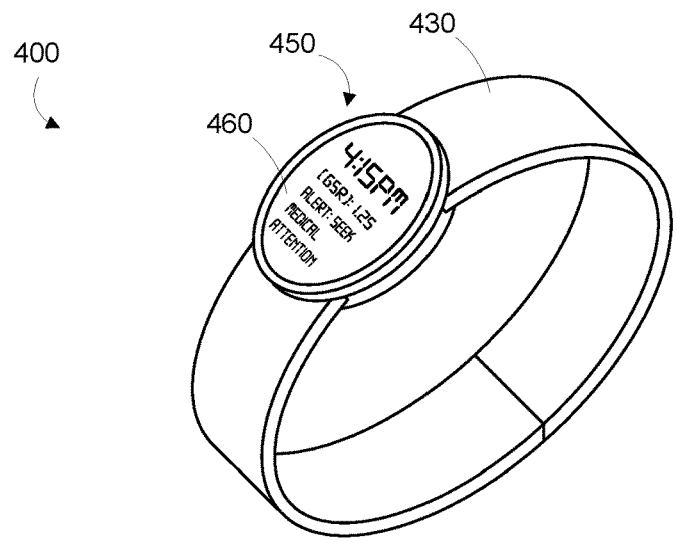
FIG. 4A is a perspective view of an example wrist-mountable device.
Figure 4B:
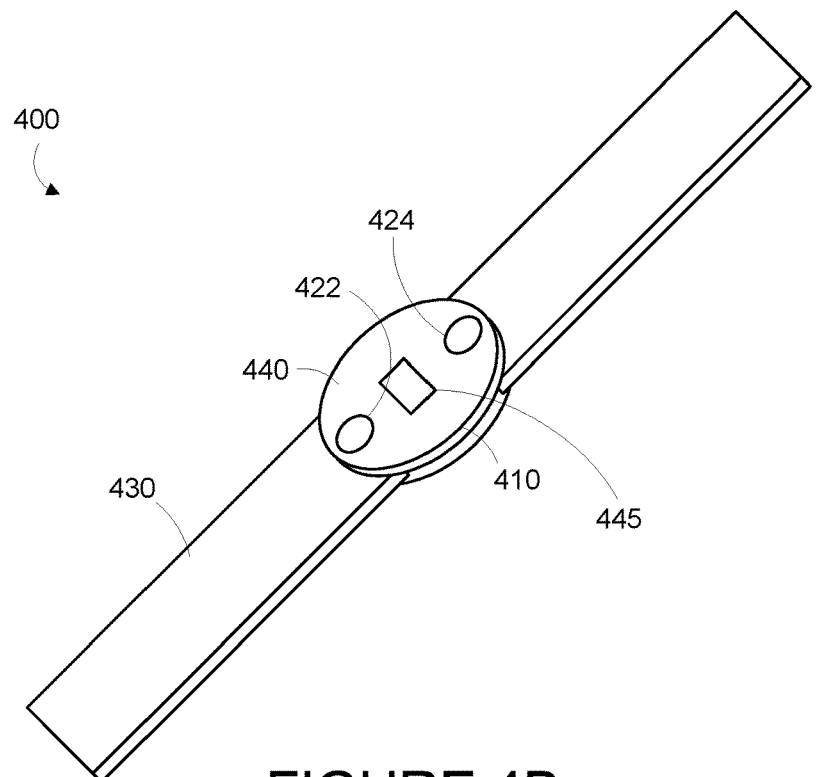
FIG. 4B is a perspective bottom view of the example wrist-mountable device shown in FIG. 4A.

In a further example shown in FIGS. 4A and 4B, a wrist mounted device 400 includes a housing 410, disposed on a strap 430. Inner face 440 of housing 410 may be positioned proximate to a body surface so that a first electrical contact 422 and a second electrical contact 424 protruding from the housing 410 may be used to measure one or more physiological parameters of the body surface proximate to the housing 410. A detector 445 for detecting at least one other physiological parameter of the wearer could also be disposed on the inner face 440 of the housing 410. A user interface 450 with a display 460 may be positioned facing outward from the housing 410. As described above in connection with other embodiments, user interface 450 may be configured to display data about the wrist mounted device 400, including whether the wrist mounted device 400 is active, a type of motion in which wrist mounted device 400 is engaged, a GSR of skin proximate to the inner face 440 of the housing 410 measured using the first and second electrical contacts 422, 424, physiological data about the wearer obtained using the detector 445, and one or more alerts generated by a remote server or other remote computing device, or a processor located on the wrist mounted device 400. In addition, the user interface 450 may display an activity metric. The activity metric could be representative of physical activity engaged in by the wearer of device 400 and could be based on physiological data about the wearer obtained using the detector 445 as well as demographical information specific to the wearer. The user interface 450 may also be configured to display the time of day, date, or other information that may be relevant to the wearer.

Figure 5:
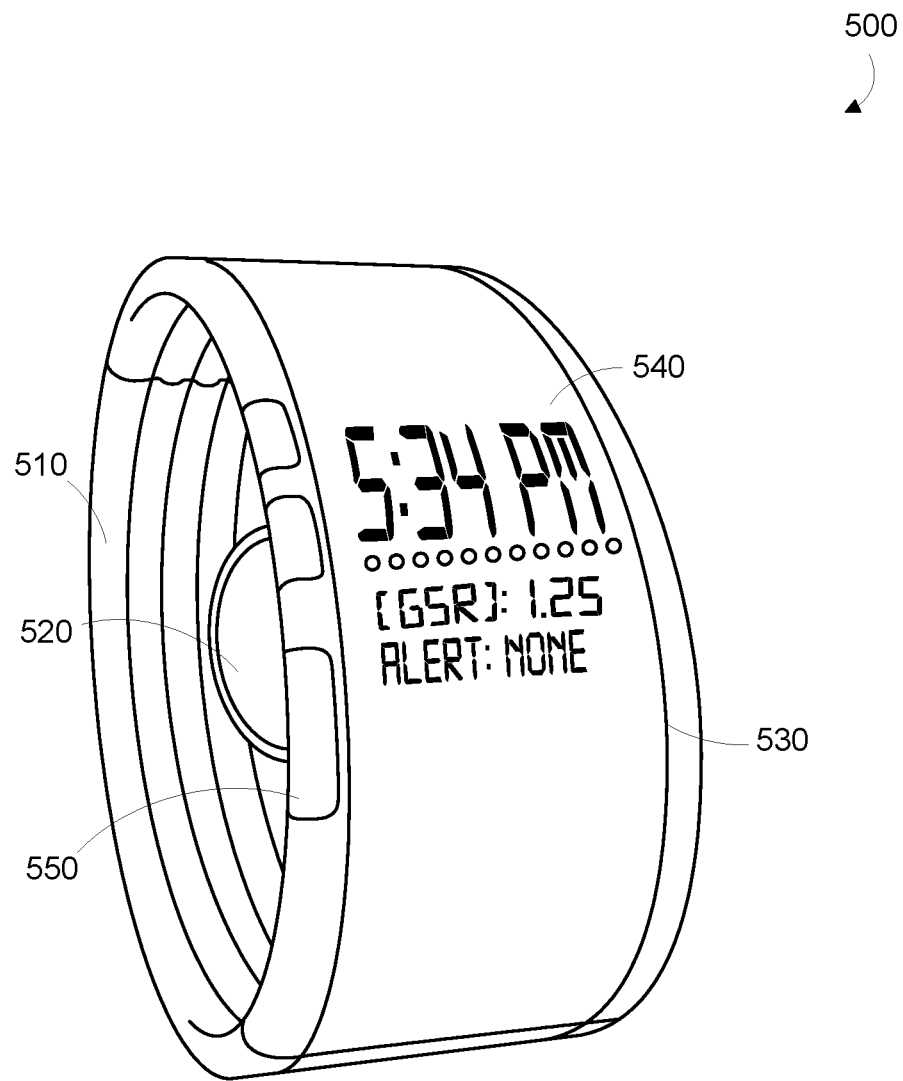
FIG. 5 is a perspective view of an example wrist-mountable device.
Figure 6:
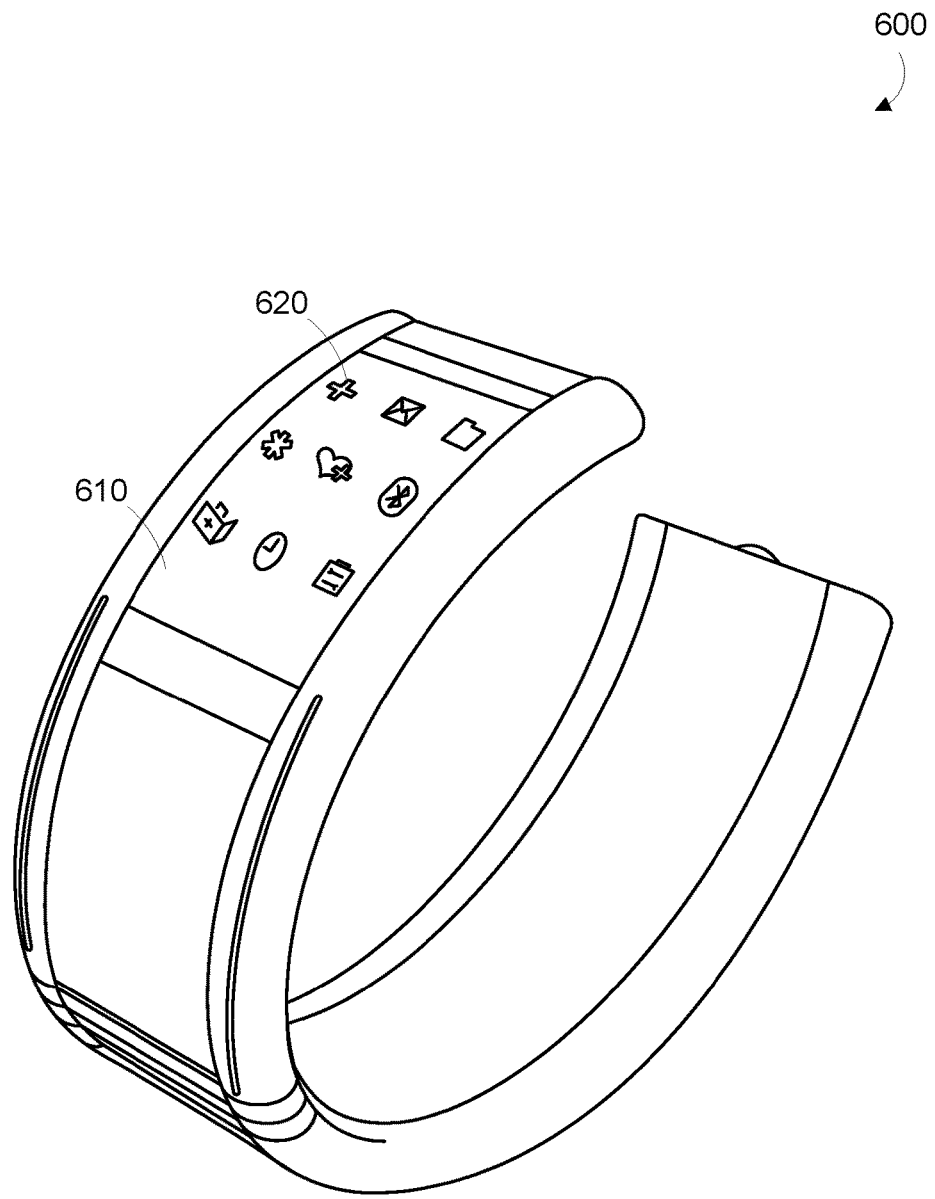
FIG. 6 is a perspective view of an example wrist-mountable device.

As shown in FIG. 5, in a further embodiment, wrist-mounted device 500 may be provided on a cuff 510. Similar to the previously discussed embodiments, device 500 includes a housing 520 and a user interface 530, which may include a display 540 and one or more buttons 550. The display 540 may further be a touch-screen display configured to accept one or more inputs by the wearer. For example, as shown in FIG. 6, display 610 may be a touch-screen configured to display one or more virtual buttons 620 for accepting one or more inputs for controlling certain functions or aspects of the device 600, or inputs of information by the user, such as current health and/or affect state.

Figure 7:
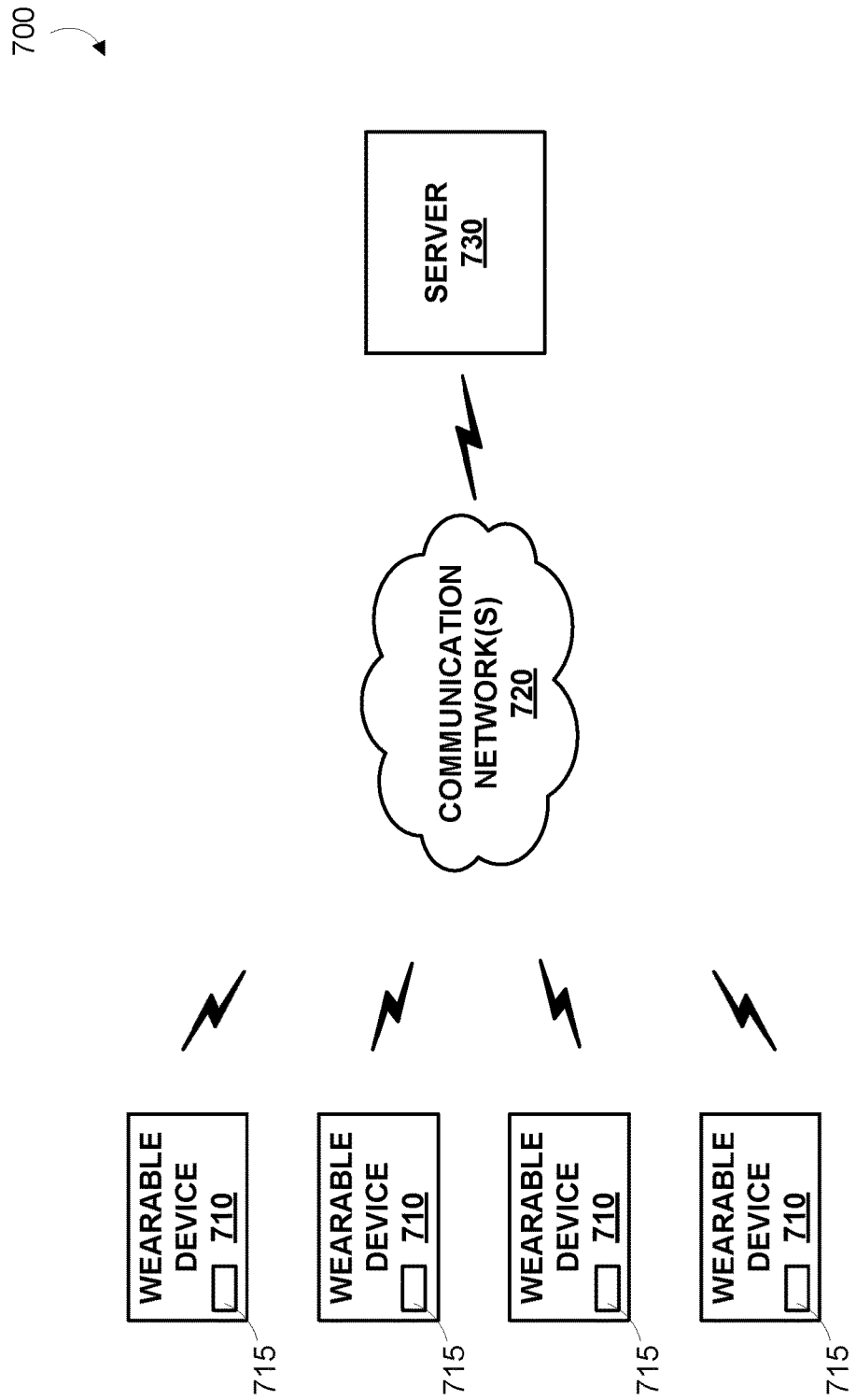
FIG. 7 is a block diagram of an example system that includes a plurality of wearable devices in communication with a server.

FIG. 7 is a simplified schematic of a system 700 including one or more wearable devices 710. The one or more wearable devices 710 may be configured to transmit data via a communication interface 715 over one or more communication networks 720 to an external device, such as remote server 730. In one embodiment, the communication interface 715 includes a wireless transceiver for sending and receiving communications to and from the server 730. In further embodiments, the communication interface 715 may include any means for the transfer of data, including both wired and wireless communications. For example, the communication interface 715 may include a universal serial bus (USB) interface or a secure digital (SD) card interface. Communication networks 720 may include any of: a plain old telephone service (POTS) network, a cellular network, a fiber network, and a data network. The server 730 may include any type of remote computing device or remote cloud computing network. Further, communication network 720 may include one or more intermediaries, including, for example wherein the wearable device 710 transmits data to a mobile phone or other personal computing device, which in turn transmits the data to the server 730.

In addition to receiving communications from the wearable device 710, such as collected physiological parameter data and data regarding health state as input by the user, the server 730 may also be configured to gather and/or receive either from the wearable device 710 or from some other source, information regarding a wearer's overall medical history, environmental factors, and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

The server 730 may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Additionally, the server 730 may be configured to gather and/or receive the date, time of day, and geographical location of each wearer of the device during each physiological parameter measurement. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

In one example, the server 730 may receive indications of when, where, and for how long a wearer of a wearable device engaged in a physical activity. For instance, when a wearer of a wearable device 710 engages in a running activity, the server 730 may receive from the wearable device 710 data that indicates the course taken by the wearer during the running activity, the duration of the running activity, and one or more physiological parameter measurements taken by the wearable device 710 at various times during the running activity, including, for example, blood pressure, pulse rate, respiration rate, skin temperature, blood-oxygen level etc. Physiological parameter data and location data may be used to facilitate other determinations as well, such as the detection and monitoring of spreading of diseases.

Additionally, the server 730 may be configured to gather and/or receive demographical data related to the wearers of wearable devices 710. In some examples, this demographical data may include data that indicates an individual wearer's age, height, weight, gender, ethnicity, occupation, residence city, state, or region, information related to a wearer's medical history, social actions, or one or more other categories of demographical data. The server may be configured to store such demographical data in one or more databases (not shown). The server may be configured to correlate physiological parameter data received from wearable devices 710 with the demographical data related to wearers of wearable devices 710 in order to provide wearable devices 710 with relevant information.

In one example, server 730 may provide wearable devices 710 with indications of an activity metric that is calculated based on the physiological parameter data and the demographical data. The activity metric may be a numeric indication of the sum total of physical activity engaged in by a wearer. The activity metric may be calculated using a formula that takes into account the physiological parameter measurements as well as the demographical data. That is, an activity metric calculation may be different for wearers associated with different demographical data. Additionally or alternatively, server 730 may be configured to provide to an individual wearable device 710 an indication of where the physiological parameter data received from the individual wearable device 710 ranks among other physiological parameter data received from other wearable devices 710. Such rankings may be global rankings in that the rankings indicate where the physiological parameter data ranks among all wearers. Additionally or alternatively, the rankings may be demographic-specific rankings in that the rankings indicate where the physiological parameter data ranks among wearers with similar demographic data. As will be appreciated from the entirety of this description, server 730 may utilize demographical data in other ways in order to provide relevant information to the wearable devices 710.

In some examples, server 730 may be configured to gather the demographical data directly from the wearable devices 710 via the communication network(s) 720. In such examples, a wearer may provide the wearable device 710 with demographical data related to the wearer by inputting the demographical data via a user interface. Alternatively or additionally, server 730 may be configured to gather the demographical data from one or more external devices communicatively coupled to communication network(s) 720 (e.g., a personal or laptop computer, a tablet computer, a mobile phone, or any other personal computing device). Other ways of gathering demographical data are possible as well.

Wearers of a wearable device may be provided with an opportunity to control whether or how the device collects demographical information about the wearer, or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Further, some embodiments of the system may include privacy controls which may be automatically implemented or controlled by the wearer of the device. For example, where a wearer's collected data are uploaded to a cloud computing network for analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Figure 8:
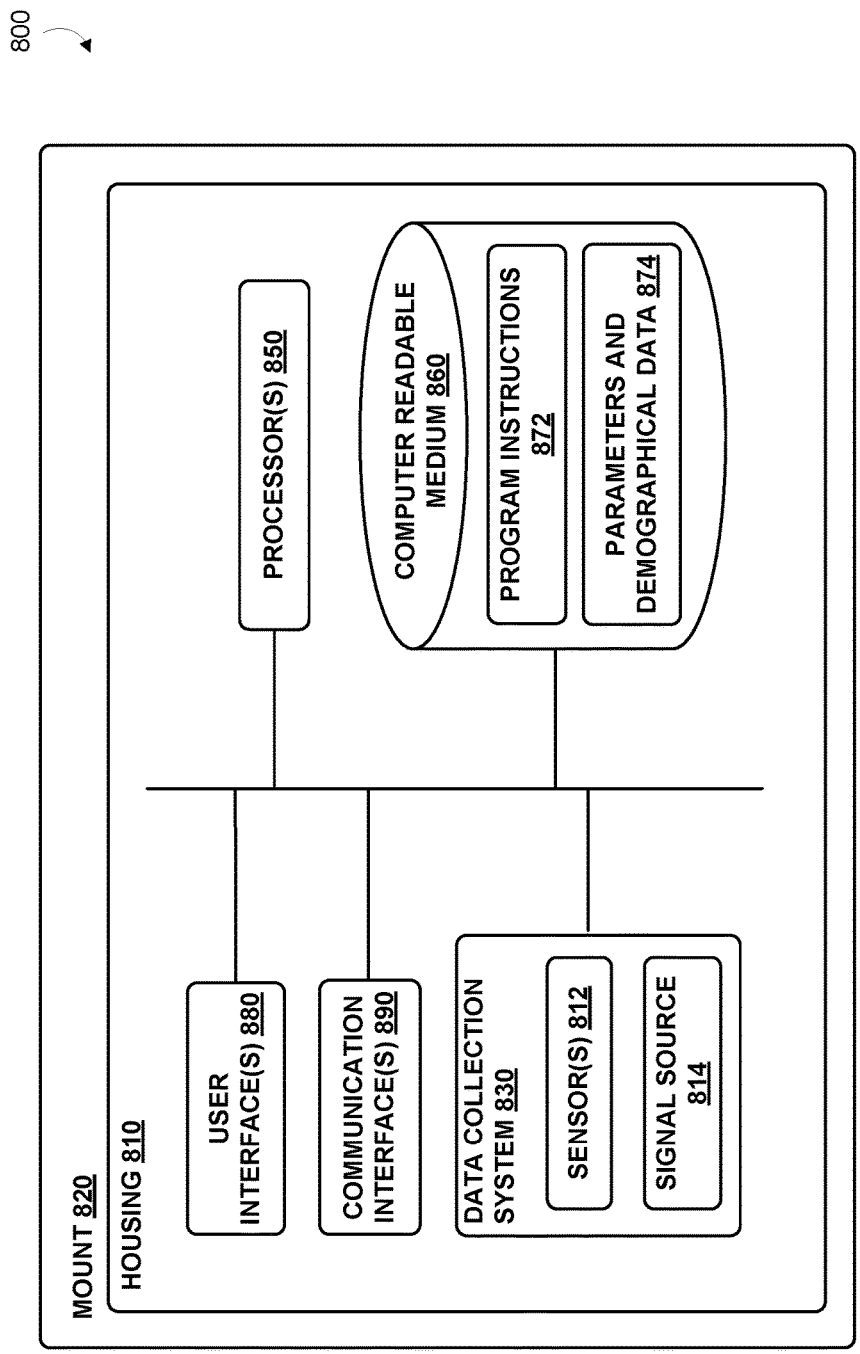
FIG. 8 is a functional block diagram of an example wearable device.

FIG. 8 is a simplified block diagram illustrating the components of a wearable device 800, according to an example embodiment. Wearable device 800 may take the form of or be similar to one of wearable device 100, 710 and/or the wrist-mounted devices 200, 300, 400, 500, 600, shown in FIGS. 1, 2A-B, 3A-3C, 4A-4C, 5, 6, and 7. However, wearable device 800 may also take other forms, for example, an ankle, waist, or chest-mounted device.

In particular, FIG. 8 shows an example of a wearable device 800 having a housing 810, and a data collection system 830 that includes sensor(s) 812 and, in some embodiments, a signal source 814. Signal source 814 may generate an interrogation signal, timing signal, and/or other signal that will produce a responsive signal that can be detected by one or more of sensor(s) 812. Sensor(s) 812 may include any sensor and/or detector capable of detecting at least one physiological parameter, which could include any parameters that may relate to the health of the person wearing the wearable device and/or the type, duration, and intensity of physical activity.

For example, sensor(s) 812 could include one or more detectors and/or sensors configured to measure physiological data, such as blood pressure, pulse rate, skin temperature, GSR, blood-oxygen level, etc. At least one of the detectors 812 is configured to non-invasively measure one or more analytes in blood circulating in subsurface vasculature proximate to the wearable device. In some examples, detector 812 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some examples, sensor(s) 812 may include one or more sensors and/or detectors configured to measure conditions in an environment about computing device 800 and provide data about that environment. The data can include, but is not limited to: data about computing device 800, location data about computing device 800, velocity (speed, direction) data about computing device 800, acceleration data about computing device 800, and other data about the environment for computing device 800. Examples of sensor(s) 812 configured to measure conditions in an environment include, but are not limited to, power sensor(s), battery sensor(s), movement sensor(s), GPS sensor(s), location sensors(s), gyroscope(s), accelerometer(s), magnetometer(s), camera(s), light sensor(s), infrared sensor(s), and microphone(s).

Processor(s) 850 may be a general-purpose processor or a special purpose processor (e.g., digital signal processors, application specific integrated circuits, etc.). The one or more processors 850 can be configured to execute computer-readable program instructions 872 that are stored in a computer readable medium 860 and are executable to provide the functionality of a wearable device 800 described herein. The computer readable medium 860 may further contain other data or information usable to provide the functionality described herein, including but not limited to, the functionality of a wearable device, associated computing device, and/or server described herein.

The computer readable medium 860 may include or take the form of one or more non-transitory, computer-readable storage media that can be read or accessed by at least one processor 850. The one or more computer-readable storage media can include volatile and/or non-volatile storage components, such as optical, magnetic, organic or other memory or disc storage, which can be integrated in whole or in part with at least one of the one or more processors 850. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

The program instructions 872 stored on the computer readable medium 860 may include instructions to perform or facilitate some or all of the device functionality described herein. For instance, program instructions 872 could include instructions to operate the electronics 830 to make a physiological parameter measurement using the sensor(s) 812 and signal source 814. The program instructions 872 could include instructions to operate based on parameter and demographical data 874 stored in the computer readable medium 860 and/or modify the parameters and demographical data 874. The program instructions 872 stored on the computer readable medium 860 could include instructions for operating the processors 850 to operate the communication interface(s) 890 to transmit the measured physiological parameters to an external device, such as a server and to receive an activity metric from the external device.

In some examples, the program instructions 872 may include instructions to calculate an activity metric based on at least some of the demographical data 874 stored in computer readable medium 860. The activity metric calculated by program instructions 872 could be a preliminary activity metric, which could be refined based on subsequent communication with an external device, such as a server. Alternatively, the activity metric calculated by program instructions 872 could be calculated by program instructions 872 without involvement of an external device.

The program instructions 872 can include instructions for operating the user interface(s) 880. For example, the program instructions 872 could include instructions for displaying data about the wearable device 800, for displaying a measured and/or determined physiological parameter or activity metric or other information obtained by the wearable device 800, or for displaying one or more alerts generated by the wearable device 800 and/or received from an external system. Further, program instructions 872 may include instructions to execute certain functions based on inputs accepted by the user interface(s) 880, such as inputs accepted by one or more buttons disposed on the user interface(s) 880.

Communication interface 890 may also be operated by instructions within the program instructions 872, such as instructions for sending and/or receiving information via an antenna, which may be disposed on or in the wearable device 800. The communication interface 890 can optionally include one or more oscillators, mixers, frequency injectors, etc. to modulate and/or demodulate information on a carrier frequency to be transmitted and/or received by the antenna. In some examples, the wearable device 800 is configured to indicate an output from the processor by modulating an impedance of the antenna in a manner that is perceivable by a remote server or other remote computing device.

In some examples, physiological parameter measurements, wearer profiles, history of wearable device use, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter measurements and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by instructions contained in the program instructions 872 that a medical condition is indicated, the wearable device 800 may generate an alert via the user interface 880. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Note that, while the user interfaces(s) 880, communication interfaces(s) 890, data collection system 830, processor(s) 850, and computer readable medium 860 are described herein as being disposed in a single housing 810, other configurations are anticipated. In some examples, a wearable device could include multiple housings (e.g., the wearable devices 100, 710 and/or the wrist-mounted devices 200, 300, 400, 500, 600, shown in FIGS. 1, 2A-B, 3A-3C, 4A-4C, 5, 6, and 7) and the components of the wearable device could be distributed amongst the multiple housings. For example, a first housing could contain at least some of the data collection system 830 (for example, one of sensor(s) 812 and/or signal source 814). A second housing could include the communication interface(s) 890, the user interface(s) 880, and/or any of the other components depicted in FIG. 8. Other numbers of housings, configurations of housings, and dispositions of components within multiple housings are anticipated.

III. EXAMPLE OPERATION OF A WEARABLE DEVICE AND SERVER

Figure 9:
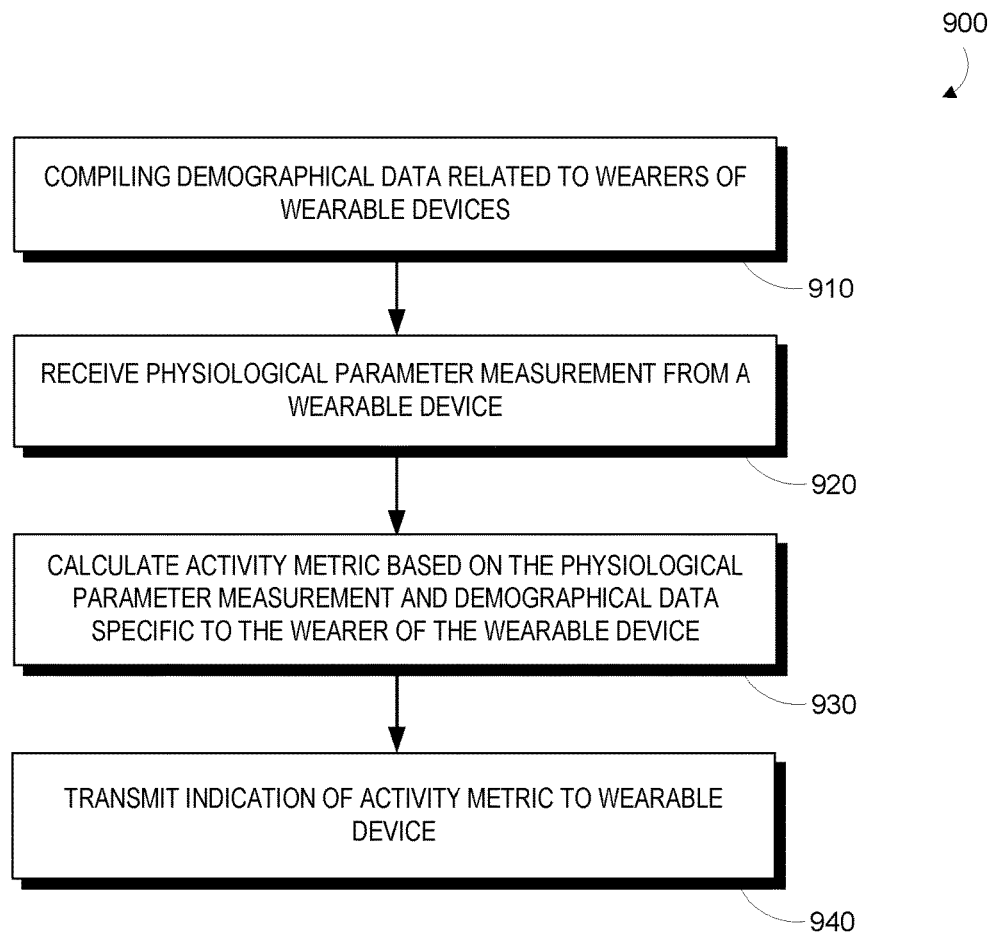
FIG. 9 is a flowchart of an example method.
Figure 10:
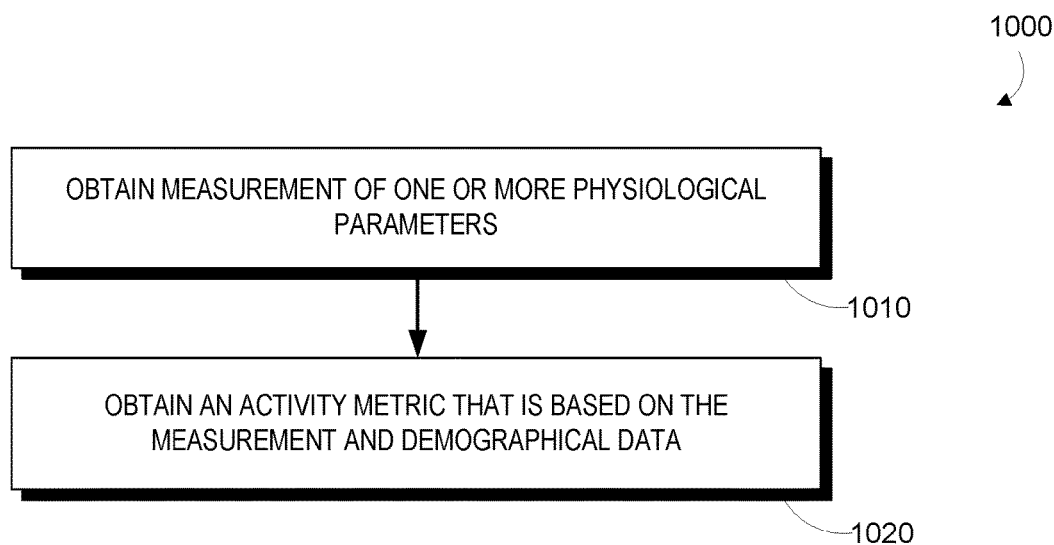
FIG. 10 is a flowchart of an example method.

FIGS. 9 and 10 are flowcharts of example methods 900 and 1000 that could be used for activity metric calculation. The example methods 900 and 1000 may include one or more operations, functions, or actions, as depicted by one or more of blocks 910, 920, 930, 940, 1010, and/or 1020, each of which may be carried out by any of the systems described by way of FIGS. 1, 2A-B, 3A-3C, 4A-4C, 5, 6, 7, and 8; however, other configurations could be used.

Furthermore, those skilled in the art will understand that the flowcharts described herein illustrate functionality and operation of certain implementations of example embodiments. In this regard, each block of each flow diagram may represent a module, a segment, or a portion of program code, which includes one or more instructions executable by a processor for implementing specific logical functions or steps in the process. The program code may be stored on any type of computer readable medium, for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

Method 900 begins at block 910 where a server compiles demographical data related to wearers of wearable devices. As indicated above, the compiled demographical data may include data assorted into one or more categories, including (but not limited to) a wearer's age, height, weight, gender, ethnicity, occupation, residence city, state, or region, information related to a wearer's medical history, or social actions. The server may be configured to store the demographical data in one or more databases coupled to or integrated with the server.

In some examples, the server may be configured to gather the demographical data from the individual wearable devices in communication with the server. In such examples, a wearer may provide a wearable device with demographical data related to the wearer by inputting the demographical data into the wearable device via a user interface. The wearable device may then transmit the demographical data to the server via wired or wireless communication over one or more communication network(s), such as the Internet. In some examples, the wearable device is configured to transmit the demographical data directly to the server, whereas in other examples the wearable device may be additionally or alternatively configured to transmit the demographical data to one or more intermediary devices (such as a mobile phone, tablet computer, or other personal computing device), which in turn may transmit the data to the server.

In some examples, the server may be configured to gather the demographical data from another personal computing device, such a wearer's mobile phone or tablet computer. In such examples, the server may be configured to establish user accounts for the individual wearable devices. A wearer may then log in to his or her user account via a personal computing device and provide and/or update demographical data specific to that wearer. Other configurations are possible as well.

Continuing at block 920, the server may receive from a wearable device one or more physiological parameter measurements related to the wearer of the wearable device. The server may receive the physiological parameter measurement from the wearable device via wired or wireless communication over one or more communication network(s), such as the Internet. In some examples, the server is configured to receive the measurement directly from the wearable device, whereas in other examples the server is additionally or alternatively configured to receive the measurement from one or more intermediary devices (such as a mobile phone, tablet computer, or other personal computing device), which may have received the measurement from the wearable device.

As described above, a wearable device may obtain a physiological parameter measurement via one or more sensors located at the wearable device. In some examples, the physiological parameter measurement may relate to the health of the wearer. For instance, the physiological parameter may be related to the blood pressure, pulse rate, respiration rate, skin temperature, GSR, or any other health-related physiological parameter. In some examples, the physiological parameter may relate to the type, duration, and intensity of physical activity engaged in by the wearer. For instance, the physiological parameter measurement may indicate that the wearer engaged in a running activity for 30 minutes on a particular date and at a particular time. The measurement may also indicate GPS coordinates of a course taken by the wearer during the physical activity, as well as perhaps indications of health-related physiological parameter measurements (e.g., blood pressure, pulse rate, respiration rate, skin temperature, GSR, etc.) of the wearer taken by the wearable device during the physical activity.

Continuing at block 930, the server calculates an activity metric that is based on the physiological parameter measurement received at block 920 and the demographical data specific to a wearer of the wearable device compiled at block 910. As described above, an activity metric may be a numeric representation of the physiological parameter and/or physical activity engaged in by a wearer. In one example, the activity metric is a representation of an estimated number of kilocalories expended by the wearer of the wearable device during the physiological parameter measurement. In another example, the activity metric is a representation of the Metabolic Equivalent of Task (MET) value for the physiological parameter measurement. In another example, the activity metric is a representation of the number of joules, watts, or other indication of energy expended during the physiological parameter measurement. And in yet another example, the activity metric may be a number of "points" awarded based on a physiological parameter measurement and the demographical data.

As mentioned, the activity metric is calculated by the server using a formula that takes into account the physiological parameter measurements as well as the demographical data. That is, an activity metric calculation may be different for wearers associated with different demographical data. Thus, when engaging in an activity metric calculation, the server may refer to the demographical data specific to the wearer of the wearable device and adjust the activity metric calculation in accordance with the demographical data. For instance, in embodiments in which the activity metric is a representation of kilocalories, METs, watts, joules, or another measurement of energy expenditure, the formula for calculating the activity metric for a wearer may be dependent on several demographic-specific variables. In some examples, the calculation is dependent on demographical data specific to the wearer's person including the age of the wearer, gender of the wearer, height of the wearer, weight of the wearer, etc. Thus, the server may refer to these categories of person-specific demographical data and adjust the activity metric calculation accordingly. In some examples, the calculation may be dependent on other variables such as the location of the wearer during the physiological parameter measurement. In such examples, the server may use the location of the wearer during the physiological parameter measurement as a basis to retrieve from a database other location-specific data such as altitude, humidity, ambient temperature, air purity levels, or another environment-specific measurement. The server may then adjust the activity metric calculation based on this information.

In embodiments in which the activity metric is calculation of points, the formula for calculating the number of points may also be based on the physiological parameter measurement and the demographical data. For instance, from time to time, the server may change or reconfigure the number of points awarded for certain physical activities based on the demographical data of the wearers engaging in those activities. In one example, the server may determine that relatively few wearers in a particular location are engaging in running activities. In order to generate more competition or encourage more exercise among wearers in the particular location, the server may engage in activity metric calculations that award more points for running activities engaged in by wearers that are in the particular location than for wearers that are in some other location. Thus, in this example, when the physiological parameter measurement received by the server at block 920 indicates that a wearer engaged in a running activity, the server may refer to the demographical data specific to the wearer to determine the location of the wearer. The server may then engage in a calculation awarding a number of points for the running activity in accordance with the determined location of the wearer.

In another example, the server may determine that, on average, wearers of a particular occupation have spent less time per week with pulse rates above a certain threshold than have wearers of some other occupation; and therefore, wearers of the particular occupation are, on average, exercising less often than wearers of the other occupation. Thus, as an incentive for wearers of the particular occupation to exercise more, the server may engage in activity metric calculations that award more points for each unit of time (e.g., each minute) that wearers of a particular occupation have a pulse rate above a certain threshold than wearers of the other occupation. Thus, in this example, when the physiological parameter measurement received by the server at block 920 indicates that a wearer had a pulse rate that was above a certain threshold for at least the unit of time, the server may refer to the demographical data specific to the wearer to determine the occupation of the wearer. The server may then engage in a calculation awarding a number of points for the duration of time the wearer had a pulse above a certain threshold in accordance with the determined occupation of the wearer. In other examples, other calculations of activity metrics that are based on the measured physiological parameters and the demographical data are possible as well.

Continuing at block 940, the server transmits an indication of the calculated activity metric to the wearable device. The server may transmit the indication of the activity metric to the wearable device via wired or wireless communication over one or more communication network(s), such as the Internet. In some examples, the server is configured to transmit the indication directly to the wearable device, whereas in other examples the server may be additionally or alternatively configured to transmit the indication to one or more intermediary devices (such as a mobile phone, table computer, or other personal computing device), which in turn may transmit the indication to the wearable device. Other configurations are possible as well. Once received at the wearable device, the wearable device may be configured to display the indication of the activity metric on a user interface.

Although not depicted by the flowchart of FIG. 9, the server may additionally or alternatively engage in one or more other functions. For example, in addition (or as an alternative) to calculating an activity metric for a wearer based on a physiological parameter measurement and demographical data specific to the wearer, the server may determine a ranking of the activity metric and/or the physiological parameter measurement. In one example, the ranking may indicate where the activity metric or physiological parameter measurement of a particular wearer ranks among activity metrics or physiological parameter measurements of other wearers with similar demographical data in one or more categories to that of the particular wearer. For instance, in examples in which the server receives resting pulse rate measurements of a particular wearer, the server may determine where the resting pulse rate measurements of the particular wearer rank among resting pulse rates of all wearers in the particular wearer's location, among wearers with similar occupations to the particular wearer, among wearers similar in age, weight, or gender, and/or among wearers having any other similarity in demographic data to the particular wearer.

In examples in which the server receives information indicating the type, duration, and intensity of a particular wearer's physical activity, the server may determine how the wearer's performance during the physical activity ranks among other wearers that have similar demographical data in one or more categories to that of the particular wearer and who engaged in a similar physical activity to that of the particular wearer. For example, if the server receives physiological parameter data indicating that a particular wearer engaged in a running activity at a particular time, in a particular location, and took a particular course, the server may determine how physiological parameter data measured during the particular wearer's running activity (e.g., pulse rate, skin temperature, or time to complete the course) ranks among other wearers in the same location who engaged in a similar running activity at a similar time, or who took a similar course, and who, perhaps, have similar occupations to the particular wearer. However, in other examples, the server may determine rankings among wearers having similar demographical data in other categories.

Upon determining such rankings, the server may transmit to the wearable devices indications of the determined rankings. The server may transmit indications of the rankings in any of the ways described above with respect to transmission of the calculated activity metric. Additionally or alternatively, the server may transmit an indication of the determined rankings (or any other determined value, such as an activity metric or physiological parameter measurement) to other entities as the wearer permits. In one example, the server may transmit indications of activity metrics, rankings, or physiological parameter measurements to a wearer's employer or insurance company in order to qualify the wearer for incentive programs such as discounts on premiums or to qualify the wearer for extra vacation days in accordance with a health-related incentive program. The server may transmit the indications of activity metrics, rankings, or physiological parameter measurements to other entities as the wearer permits as well.

Turning now to FIG. 10, method 1000 begins at block 1010 where a wearable device obtains a measurement of one or more physiological parameters related to a wearer of the wearable device. As described above, a wearable device may obtain a physiological parameter measurement via one or more sensors located at the wearable device. In some examples, the physiological parameter measurement may relate to the health of the wearer. For instance, the physiological parameter may be related to the blood pressure, pulse rate, respiration rate, skin temperature, GSR, or any other health-related physiological parameter. In some examples, the physiological parameter may relate to the type, duration, and intensity of physical activity engaged in by the wearer. For instance, the physiological parameter measurement may indicate that the wearer engaged in a running activity for 30 minutes on a particular date and at a particular time. The measurement may also indicate GPS coordinates of a course taken by the wearer during the running activity, as well as perhaps indications of health-related physiological parameter measurements (e.g., blood pressure, pulse rate, respiration rate, skin temperature, GSR, etc.) of the wearer taken by the wearable device during the running activity.

Continuing at block 1020, the wearable device obtains an activity metric that is based on the measurement of one or more physiological parameters related to the wearer and on demographical data that is specific to the wearer. The activity metric could be a numeric value or other indication that is representative of an extent of physical activity engaged in by the wearer. The wearable device may obtain the activity metric in various ways. In approach, the wearable device may calculate the activity metric on its own. In another approach, the wearable device may receive the activity metric from an external device, such as a server, which calculates the activity metric using one or more physiological parameter measurements provided by the wearable device.

Thus, block 1020 may involve the wearable device transmitting the obtained measurement of one or more physiological parameters to the external device. The wearable device may transmit the measurements to the server via wired or wireless communication over one or more communication network(s), such as the Internet. In some examples, the wearable device is configured to transmit the measurements directly to the server, whereas in other examples the wearable device may be additionally or alternatively configured to transmit the measurements to one or more intermediary devices (such as a mobile phone, table computer, or other personal computing device), which in turn may transmits the measurements to the server. Other configurations are possible as well.

Block 1020 may further involve the wearable device receiving from the external device an indication of an activity metric that is based on the measurement transmitted by the wearable device and demographical data specific to the wearer of the wearable device. The wearable device may receive an indication of an activity metric in the same way as the wearable device transmitted the physiological parameter measurement. That is, the wearable device may receive the indication of the activity metric via wired or wireless communication over one or more communication network(s), such as the Internet. In some examples, the wearable device is configured to receive the activity metric directly from the server, whereas in other examples the wearable device may be additionally or alternatively configured to receive the activity metric from one or more intermediary devices (such as a mobile phone, table computer, or other personal computing device), which may have received the activity metric from the server. Other configurations are possible as well.

Although not depicted by the flowchart of FIG. 10, the wearable device may additionally or alternatively engage in one or more other functions. For example, prior to receiving from the external device an indication of an activity metric, the wearable device may engage in a preliminary calculation of an activity metric based on the physiological parameters measured at the wearable device and demographical data stored in data storage at the wearable device and specific to a wearer of the wearable device. The preliminary activity metric calculation may be the same calculation engaged in by the external device or the preliminary activity metric calculation may be based on a smaller subset of demographical data than the calculation engaged in by the external device.

Method 1000 may further involve the wearable device providing an indication of the activity metric and/or preliminary activity metric via a user interface. The indication of the activity metric may include a visual indication of the activity metric, for example, using text and/or graphics on a display. Alternatively or additionally, the indication of the activity metric may include an auditory or tactile indication.

IV. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A method comprising:
    obtaining, via a wearable device, a measurement of one or more physiological parameters related to a wearer of the wearable device;
    in response to obtaining the measurement, transmitting, via the wearable device, the measurement to an external device;
    calculating, by the wearable device, a preliminary activity metric based on the obtained measurement of the one or more physiological parameters;
    indicating to the wearer, by the wearable device, the preliminary activity metric;
    receiving, via the wearable device, a subsequent activity metric from the external device, wherein the subsequent activity metric is based on both (i) the obtained measurement of the one or more physiological parameters and (ii) demographical data specific to the wearer; and refining the preliminary activity metric based on the received subsequent activity metric, the refining including indicating to the wearer, by the wearable device, the refined activity metric.

2. The method of claim 1, wherein both the preliminary activity metric and the subsequent activity metric are numeric values that are representative of an extent of physical activity engaged in by the wearer.

3. The method of claim 1, wherein the measurement of one or more physiological parameters comprises a measurement of one or more of the following: a pulse, a blood-oxygen level, a Galvanic skin resistance (GSR), a skin temperature, or data from a motion sensor in the wearable device.

4. The method of claim 1, wherein the demographical data comprises data related to one or more of the following: an age, a gender, a weight, an ethnicity, an occupation, or a location.

5. The method of claim 1, wherein the subsequent activity metric is further based on data related to a medical history of the wearer.

6. The method of claim 5, wherein the medical history of the wearer comprises data regarding the wearer's health state from a hospital or physician.

7. The method of claim 1, wherein the subsequent activity metric comprises an activity-metric ranking based on where the subsequent activity metric ranks among other activity metrics calculated for a plurality of other wearers of other wearable devices.

8. The method of claim 7, wherein the plurality of other wearers have demographical data in one or more categories similar to the demographical data specific to the wearer of the wearable device.

9. A wearable device, comprising:
one or more sensors configured to measure physiological parameters related to a wearer of the wearable device; and
one or more processors configured to perform functions comprising:
causing the one or more sensors to obtain a measurement of at least one physiological parameter;
transmitting the obtained measurement to an external device;
calculating a preliminary activity metric based on the obtained measurement of the one or more physiological parameters;
indicating the preliminary activity metric to the wearer;
receiving, from the external device, a subsequent activity metric, wherein the subsequent activity metric is based on both (i) the obtained measurement of the at least one physiological parameter and (ii) demographical data specific to the wearer; and
refining the preliminary activity metric based on the received subsequent activity metric, the refining including indicating the refined activity metric to the wearer.

10. The wearable device of claim 9, wherein both the preliminary activity metric and the subsequent activity metric are numeric values that are representative of an extent of physical activity engaged in by the wearer.

11. The wearable device of claim 9, wherein the measurement of one or more physiological parameters comprises a measurement of one or more of the following: a pulse, a blood-oxygen level, a Galvanic skin resistance (GSR), a skin temperature, or data from a motion sensor in the wearable device.

12. The wearable device of claim 9, wherein the demographical data comprises data related to one or more of the following: an age, a gender, a weight, an ethnicity, an occupation, or a location.

13. The wearable device of claim 9, wherein the subsequent activity metric comprises an activity-metric ranking based on where the subsequent activity metric ranks among other activity metrics calculated for a plurality of other wearers of other wearable devices.

14. The wearable device of claim 13, wherein the plurality of other wearers have demographical data in one or more categories similar to the demographical data specific to the wearer of the wearable device.

15. A non-transitory computer-readable medium having stored thereon program instructions that upon execution by a processor, cause performance of a set of operations comprising:
obtaining, via a wearable device, a measurement of one or more physiological parameters related to a wearer of the wearable device;
in response to obtaining the measurement, transmitting, via the wearable device, the measurement to an external device;
calculating a preliminary activity metric based on the obtained measurement of the one or more physiological parameters;
indicating the preliminary activity metric to the wearer;
receiving, via the wearable device, a subsequent activity metric from the external device, wherein the subsequent activity metric is based on both (i) the obtained measurement of the one or more physiological parameters and (ii) demographical data specific to the wearer; and
refining the preliminary activity metric based on the received subsequent activity metric, the refining including indicating to the wearer, via the wearable device, the refined activity metric.

16. The non-transitory computer-readable medium of claim 15, wherein both the preliminary activity metric and the subsequent activity metric are numeric values that are representative of an extent of physical activity engaged in by the wearer.

17. The non-transitory computer-readable medium of claim 15, wherein the measurement of one or more physiological parameters comprises a measurement of one or more of the following: a pulse, a blood-oxygen level, a Galvanic skin resistance (GSR), a skin temperature, or data from a motion sensor in the wearable device.

18. The non-transitory computer-readable medium of claim 15, wherein the demographical data comprises data related to one or more of the following: an age, a gender, a weight, an ethnicity, an occupation, or a location.

19. The non-transitory computer-readable medium of claim 15, wherein the subsequent activity metric comprises an activity-metric ranking based on where the subsequent activity metric ranks among other activity metrics calculated for a plurality of other wearers of other wearable devices.

20. The non-transitory computer-readable medium of claim 19, wherein the plurality of other wearers have demographical data in one or more categories similar to the demographical data specific to the wearer of the wearable device.

* * * * *